United States Patent [19]

Thies et al.

[11] 4,158,061
[45] Jun. 12, 1979

[54] 2,9-DIOXATRICYCLO[4,3,1,0³,⁷] DECANE DERIVATIVES, PROCESSES FOR THEIR PREPARATION AND PHARMACEUTICAL COMPOSITIONS THEREOF

[75] Inventors: Peter W. Thies; Samuel David, both of Hanover, Fed. Rep. of Germany

[73] Assignee: Kali-Chemie Pharma GmbH, Hanover, Fed. Rep. of Germany

[21] Appl. No.: 897,802

[22] Filed: Apr. 19, 1978

Related U.S. Application Data

[60] Division of Ser. No. 826,681, Aug. 22, 1977, Pat. No. 4,117,148, which is a continuation-in-part of Ser. No. 770,055, Feb. 18, 1977.

[30] Foreign Application Priority Data

Feb. 21, 1976 [DE] Fed. Rep. of Germany ....... 2607106

[51] Int. Cl.² ............................................ A61K 31/335
[52] U.S. Cl. ................................. 424/278; 260/340.3
[58] Field of Search ....................... 260/340.3; 424/278

[56] References Cited

U.S. PATENT DOCUMENTS

| | | | |
|---|---|---|---|
| 4,016,176 | 4/1977 | Thies | 260/340.3 |
| 4,089,971 | 5/1978 | Thies | 424/278 |

*Primary Examiner*—Ethel G. Love
*Attorney, Agent, or Firm*—Schwartz, Jeffery, Schwaab, Mack, Blumenthal & Koch

[57] ABSTRACT

3-Azidomethyl-2,9-dioxatricyclo[4,3,1,0³,⁷] decane derivatives are disclosed which exhibit analgesic, as well as antipyretic and antiphlogistic properties, and which have the formula (I)

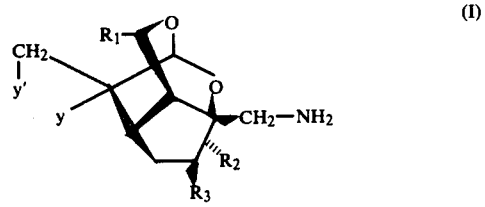

wherein:

$R_1$ represents alkyloxy or aralkyloxy;

one of $R_2$ and $R_3$ is hydrogen and the other represents hydroxy, acyloxy or carbamyloxy, or $R_2$ and $R_3$ jointly represent oxygen; and, y and y' each represent hydrogen or jointly form a bond, as well as pharmaceutical formulations thereof.

By reducing the 3-azidomethyl compounds of formula (I), the corresponding 3-aminomethyl compounds are obtained which possess sedative properties and which are valuable intermediates for preparing 3-(mono- or dialkylaminomethyl)-2,9-dioxatricyclo[4,3,1,0³,⁷] decanes which exhibit sedative and soporific activities.

9 Claims, No Drawings

2,9-DIOXATRICYCLO[4,3,1,0³,⁷] DECANE DERIVATIVES, PROCESSES FOR THEIR PREPARATION AND PHARMACEUTICAL COMPOSITIONS THEREOF

CROSS-REFERENCE TO RELATED APPLICATION

The present application is a division application of copending application Ser. No. 826,681, filed on Aug. 22, 1977, now U.S. Pat. No. 4,117,148, which is a continuation-in-part application of co-pending application Ser. No. 770,055, filed on Feb. 18, 1977, the disclosure of which is incorporated herein by reference.

BACKGROUND OF THE INVENTION

The invention relates to 3-azidomethyl-2,9-dioxatricyclo[4,3,1,0$^{3,7}$] decane derivatives and processes for their preparation and pharmaceutical compositions thereof, and also to processes for transforming them into 3-aminomethyl-2,9-dioxatricyclo[4,3,1,0$^{3,7}$] decane derivatives.

The German Offenlegungsschrifts No. 1,961,433, 2,027,890, 2,129,507, and 2,306,118 and the corresponding U.S. Pat. No. 3,812,154 and 3,917,651 disclose 2,9-dioxatricyclo[4,3,1,0$^{3,7}$] decanes which possess central nervous system depressing, narcotic, neuroleptica-like and vasodilative activities. The German Offenlegungschrift No. 2,547,205 discloses 2,9-dioxatricyclo[4,3,1,0$^{3,7}$] decanes which possess analgesic and sedative properties.

SUMMARY OF THE INVENTION

It is an object of the present invention to provide pharmacologically active 2,9-dioxatricyclo[4,3,1,0$^{3,7}$] decane derivatives which exhibit analgesic properties, as well as antipyretic and antiphlogistic properties, and are low in toxicity.

It is a further object of the present invention to provide pharmaceutical solid or liquid formulations containing 3-azidomethyl-2,9-dioxatricyclo[4,3,1,0$^{3,7}$] decane derivatives.

It is a further object of the present invention to provide a method for the treatment or prevention of pains, inflammatory processes and oedema.

It is still a further object of the present invention to provide processes for preparing primary and secondary 3-aminomethyl-2,9-dioxatricyclo[4,3,1,0$^{3,7}$] decane derivatives, especially processes which provide for obtaining such compounds in good yields.

In order to accomplish the foregoing objects according to the present invention, there are provided pharmacologically active 3-azidomethyl-2,9-dioxatricyclo[4,3,1,0$^{3,7}$] decane derivatives of the formula (I)

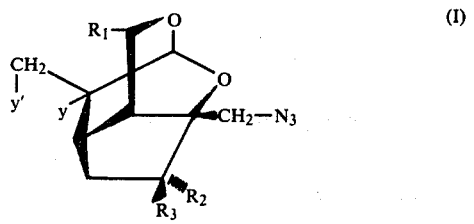

wherein:
R$_1$ represents alkyloxy or aralkyloxy;

one of R$_2$ and R$_3$ is hydrogen and the other represents hydroxy, acyloxy or carbamyloxy or R$_2$ and R$_3$ jointly represent oxygen; and y and y' each represent hydrogen or jointly form a bond.

Surprisingly, it has been found that by introducing the azido-group into the 3'-position of the known 2,9-dioxatricyclo[4,3,1,0$^{3,7}$] decane structure, analgesic compounds which also exhibit antiphlogistic and/or antipyretic properties are obtained.

Within the formula (I), the substituent in the 4-position of the 3-azidomethyl-2,9-dioxatricyclo[4,3,1,0$^{3,7}$] decanes of formula (I) preferably is hydroxy or lower acyloxy or lower carbamyloxy, most preferably acetoxy or methylcarbamyloxy. The substituent in the 8-position of 2,9-dioxatricyclo[4,3,1,0$^{3,7}$] decane preferably is a lower alkoxy group, especially methoxy, ethoxy, or butoxy. If the substituent in the 8-position is aralkyloxy, it preferably is benzyloxy. The substituent in the 10-position preferably is β-methyl.

According to the present invention, there are further provided processes for preparing the compounds of formula (I).

The compounds of formula (II)

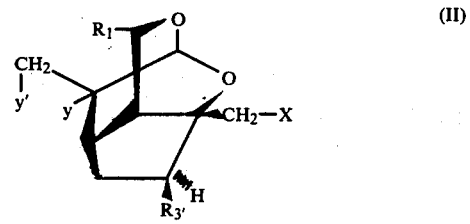

wherein X is chlorine, bromine or iodine, R$_1$ is as defined above, and R$_3$, represents acyloxy, are transferred into the corresponding azides. After introducing the azido group, the substituent in the 4-position may be further changed in order to obtain any of the above defined substituents R$_2$ and R$_3$.

According to the present invention, there are further provided pharmaceutical compositions comprising the above described compounds of formula (I), and optionally an inert diluent.

According to the present invention, there is further provided a process for preparing 3-aminomethyl-2,9-dioxatricyclo[4,3,1,0$^{3,7}$] decanes of formula (XL)

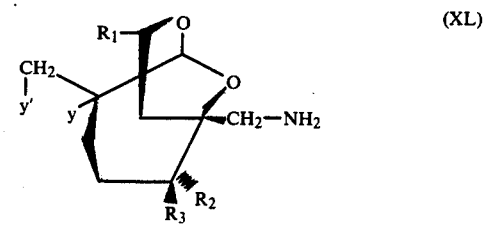

wherein R$_1$, R$_2$, R$_3$, y and y' are as defined above, which comprises the step of reducing a compound of formula (I).

The compounds of formula (XL) exhibit sedative properties and also are valuable intermediates for preparing compounds of formula (XLI)

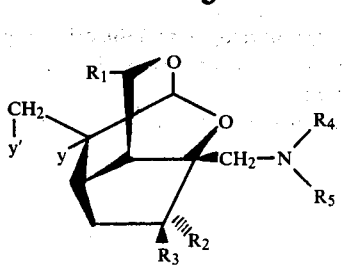

(XLI)

wherein $R_1$, $R_2$, $R_3$, y and y' are as defined above; $R_4$ represents hydrogen or alkyl; and, $R_5$ represents alkyl or, if $R_4$ is hydrogen, also represents a $CH_2$—$R_6$-group, wherein $R_6$ is alkyl or aralkyl, and which exhibit sedative properties, especially sleep promoting properties, and therefore, are useful in medical treatments, in particular, as sedatives and soporific agents in the treatment of sleep disorders.

According to the present invention, there are further provided processes for preparing the compounds of formula (XLI) by substituting the compounds of formula (XL).

Further objects, features and advantages of the present invention will become apparent from the detailed description of the invention which follows:

DETAILED DESCRIPTION OF THE INVENTION

The new compounds of formula (I) according to this invention exhibit valuable pharmacological properties and therefore are useful in medical treatment. In particular, they are useful as analgesic, antiphlogistics and antipyretics, since they exhibit analgesic activities, as well as antiphlogistic and antipyretic activities as is indicated in standard tests in animals, e.g., inhibition of the phenyl benzoquinone syndrom in mice upon oral administration of from 3 to 60 mg/kg body weight.

The pharmacological activity of the compounds of formula (I) are superior to that of commercial products which exhibit a similar pharmacological profile, as can be seen from the comparative pharmacological data which are given in Table II below.

The toxicity of the 3-azidomethyl-2,9-dioxatricyclo[4,3,1,0$^{3,7}$] decanes of the formula (I) is extremely low. The $LD_{50}$ in mice is in the range of between about 500 and about 700 mg/kg, when determined after i.p. administration of the compounds. For example, the following $LD_{50}$ values have been determined with the compounds in Table I below:

TABLE I

| Compound No. | Example No. | $LD_{50}$ mg/kg i.p. mice |
|---|---|---|
| X | 3.2.1 | 739 |
| XVIII | 5.2.1 | 632 |
| XXII | 6.2.1 | 571 |
| XXVI | 7.1.2 | 574 |

The analgesic activity of the compounds of formula (I) have been evaluated in mice using the phenyl benzoquinone syndrome (writhing test: evaluation of the analgesic activity by determining its activity in inhibiting the pain which is chemically induced by means of phenyl benzoquinone according to the method of E. Siegmund, R. Cadmus, G. Lu, Proc. Soc. expt. Biol. Med. 95, 729 (1957). The antiphlogistic/analgesic properties have been proved in rats in the Randall-Selitto-Test (evaluation of analgesic properites by determining the pressure pain threshold in the rat's paw), Real Lexikon der Medizin, Vol. 5, Urban and Schwarzenberg, 1973.

The test results are shown in the following Table II.

TABLE II

Compound of formula

| | Analgesic activity inhibition of PBC-syndrome $ED_{50}$ mg/kg mouse p.o. | Randall Selitto-test $ED_{50}$ mg/kg rat s.c. | |
|---|---|---|---|
| (Comp. No. Ex. No.) | | oedema bearing paw | normal paw |
| $R_2$=H, $R_3$=OAc $R_1$=OMe, y=10$\beta$-$CH_3$ (X, 3.2.1) | ~10 | >32 | >32 |
| $R_2$+$R_3$=O $R_1$=OMe, y=10$\beta$-$CH_3$ (XVIII, 5.2.1) | <56 | >100 | >100 |
| $R_2$=OH, $R_3$=H $R_1$=OMe, y=10$\beta$-$CH_3$ (XXII, 6.2.1) | 18.5 | >32 | >32 |
| $R_2$=OAc, $R_3$=H $R_1$=OMe, y=10$\beta$-$CH_3$ (XXVI, 7.1.2) | <3.2 | 15 | ~32 |
| $R_2$=OAc, $R_3$=H $R_1$=OMe, y=10=$CH_2$ (XXV, 7.1.1) | ~56 | 100 | 100 |
| Comparative compounds | | | |
| Phenylbutazone | >30 | 58 | >100 |
| Aspirin | 240 | 440 | >700 |
| Indomethazine | | 64 | 250 |
| Naproxene | 30 | 147 | 250 |

As can be seen from the data in Table II, the effective dosages of the 3-azidomethyl-2,9-dioxatricyclo[4,3,1,0$^{3,7}$] decanes are considerably less than those of the comparative commercial products, e.g., several of the ED$_{50}$ values are about ten times less than those of the commercial products.

For the above-mentioned therapeutic uses of the 3-azidomethyl-2,9-dioxatricyclo[4,3,1,0$^{3,7}$] decanes, the administered doses can vary considerably depending on the type of the compound, the animal, the mode of administration, the treated condition and the therapy which is desired. Usually, satisfactory results are obtained with dosages between 0.3 and 60 mg/kg body weight. These dosages can be administered enterally, preferably orally, or parenterally. For example, daily oral dosages for larger mammals can be chosen between 0.5 and 50 mg, conveniently administered in 2 to 4 divided doses or in sustained release form.

According to a further feature of the invention, there are provided pharmaceutical compositions containing at least one of the compounds of formula (I) or their pharmaceutically acceptable salts. The compositions may take the form of solid or liquid formulations for enteral, preferably oral, or for parenteral administration. Thus, the formulations may be in the form of capsules, tablets, coated tablets, suppositories, emulsions or solutions. These formulations may comprise conventional pharmaceutical carriers. e.g., solids, such as starch, lactose, mannit, polyvinyl pyrrolidone or liquids such as sterile water, pharmaceutically acceptable alcohols or fatty oils, and may further comprise pharmaceutical adjuvants, e.g., binders or lubricants for tabletting, stabilizing, flavoring or emulsifying agents.

The compounds of formula (I) are prepared as follows:

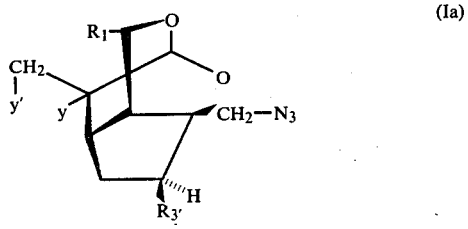

(Ia)

wherein R$_1$, R$_3'$, y and y' are as defined above, are prepared by reacting a compound of formula (II) with an alkali azide in the presence of a solvent.

The transformation of the 3-halogenomethyl group of a compound of formula (II) into the 3-azidomethyl group can be effected in a conventional manner, e.g., by reacting the compound of formula (II), which preferably is a 4-acetoxy-3-iodomethyl compound, with an alkali azide, preferably sodium azide in an aprotic polar solvent, preferably hexamethyl phosphor acid triamide, or dimethylformamide. The reaction preferably is effected at an elevated temperature, e.g., a temperature up to about 200° C., preferably a temperature of between about 80° and about 150° C.

Subsequent to the introduction of the azido group into the compound of formula (II), the substituent in the 4-position may be further changed in order to obtain any of the above defined substituents R$_2$ and R$_3$.

Thus, the compound of formula (Ia) may be hydrolyzed in a conventional manner to form the corresponding 4β-hydroxy compound of formula (Ib), wherein R$_1$, y and y' are as defined above and which may be oxidized into the 4-keto compound of formula (Ic), wherein R$_1$, y and y' are as defined above,

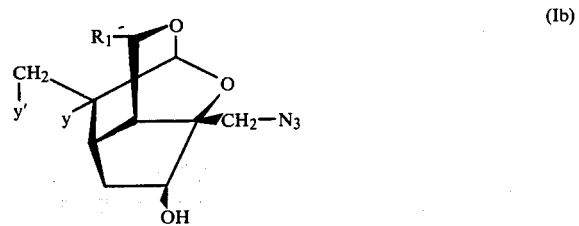

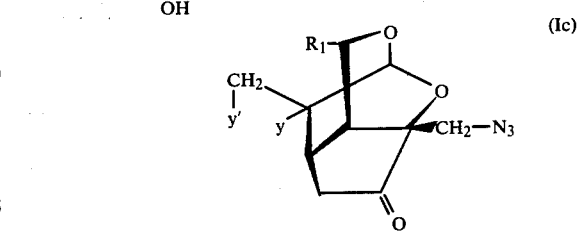

and which in turn may be reduced with a metal hydride, e.g., Li(AlH$_4$) to give the 4α-hydroxy compound of formula (Id)

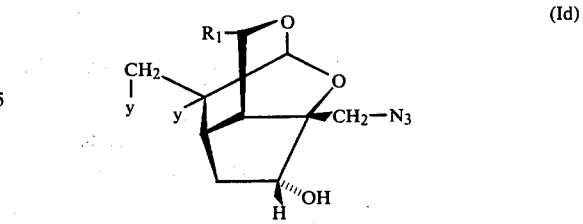

wherein R$_1$, y and y' are as defined above.

The transformation of the 4β-hydroxy compound into the 4α-hydroxy compound by way of the intermediate 4-keto compound may be performed according to the general reaction sequence which is shown below.

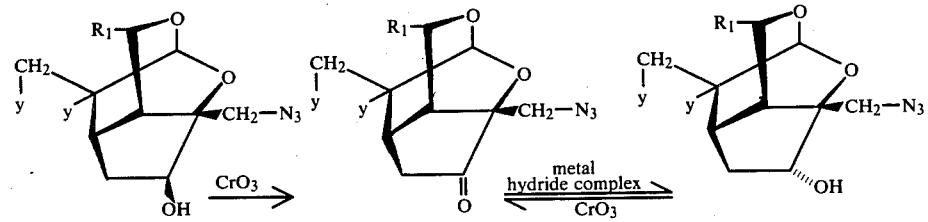

This transformation may be performed according to the methods as described in the German Offenlegungsschrift No. 2,547,205, the disclosure of which is hereby incorporated by reference.

For example, the 4β-hydroxy compound is oxidized into the decanone by means of a chromium trioxide oxidizing agent in ether or acetone. The selective reduction of the keto group in the decanone into the α-hydroxy group without effecting the azido group, can be done by means of a complex metal hydride. Lithium borohydride has been found to be a particularly suitable reducing agent.

The hydroxy group can be further transformed into an acyloxy or carbamyloxy group. For example, compounds of

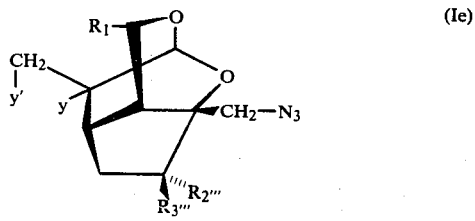

wherein $R_1$, y and y' are as defined in formula (I), and one of $R_{2'''}$ and $R_{3'''}$ is hydrogen and the other represents acyloxy or carbamyloxy, can be prepared by esterifying a compound of formula (If)

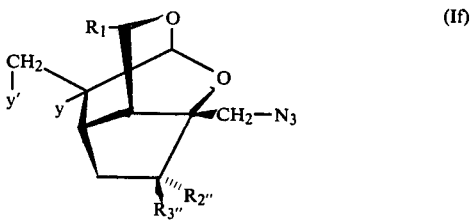

wherein $R_1$, y and y' are as defined in formula (I), and one of $R_{2''}$ and $R_{3''}$ is hydrogen and the other is hydroxyl.

The esters are prepared by conventional methods, e.g., reacting the alcohols of formula (If) with appropriate acid halides or isocyanates, respectively.

The starting compounds of formula (II) may be prepared according to the general reaction sequence which is shown below:

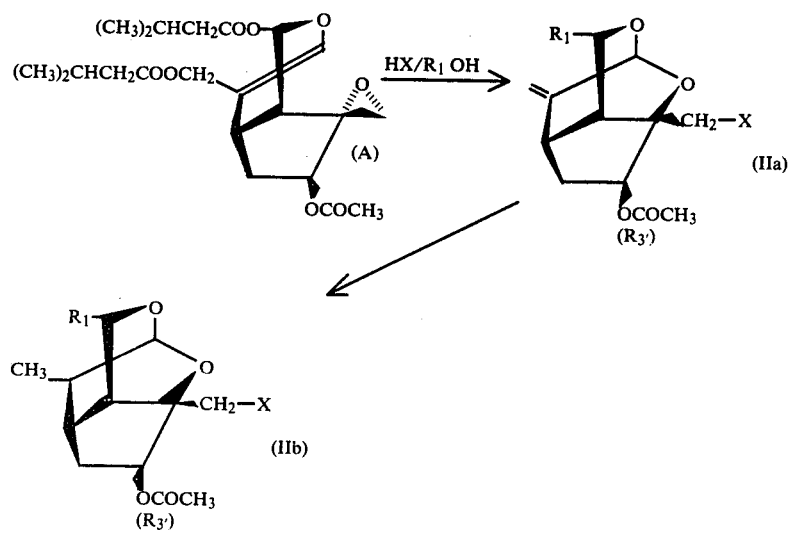

As is demonstrated in the above reaction sequence in a first step dihydrovaltratum of formula (A), or an extract containing dihydrovaltratum is reacted with a hydrogen halide HX in an alochol $R_1OH$, wherein $R_1$ is as defined above, whereby a mixture of two isomeric compounds of formula (IIa) are formed. If desired, the acetoxy group may then be transformed into another lower acyloxy group $R_{3'}$. The formation of the compounds (IIa) can be effected according to the method which is disclosed in the German Offenlegungsschrift No. 2,129,507, the disclosure of which is hereby incorporated by reference.

The hydrogenation of the 10,11-double bond in the compounds of formula (IIa) can be effected by means of hydrogen in the presence of a platinum oxide catalyst in known manners. For example, the reaction is effected in a solvent, preferably acetic acid ethyl ester or ethanol, without affecting the halogen substituents in the 3'-position. 4-acetoxy-3-iodomethyl compounds are preferred starting materials, because the 10β-methyl-3-iodomethyl-4-acetoxy compounds crystallize particularly easily from methanol and thus can be easily separated from the hydrogenation product which is a mixture of the epimeric 10α-methyl- and 10β-methyl compounds containing about 10% of the 10α-methyl epimer.

According to the present invention there are also provided processes for preparing compounds of formula (XL) and (XLI).

The primary amines of formuls (XL) are prepared by reducing a compound of formula (I).

The reduction is performed by conventional methods, preferably by means of hydrazine, in the presence of Raney nickel The primary amines of formula (XL) may be alkylated in conventional manners in order to obtain secondary or tertiary amines.

The secondary amino compounds of formula (XLIa)

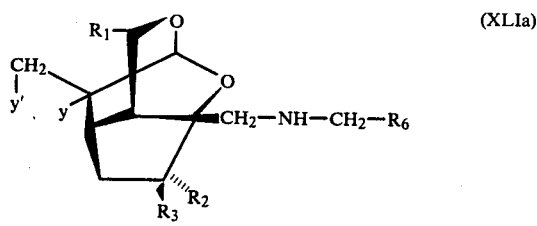

wherein $R_1$, $R_2$, $R_3$, $R_6$, y and y' are as defined in formula (XLI) which can be prepared by reacting a compound of formula (XL) with an active derivative of an acid R₆-COOH, which is selected from the group of acid halides and acid anhydrides and subsequently reducing the resulting amides.

Secondary and tertiary alkyl amino compounds of formula (XLIb)

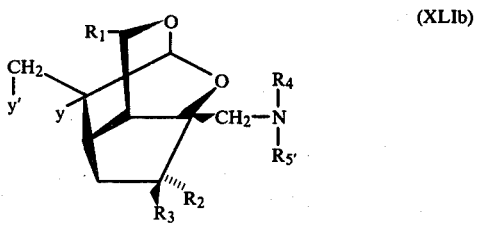

(XLIb)

wherein $R_1$, $R_2$, $R_3$, $R_4$, y and y' are as defined in formula (XLI) and $R_5$, represents alkyl, can be prepared by alkylating a compound of formula (XL) by reacting it with an aldehyde $R_{5'}=O$ under reducing conditions according to known methods. Depending on the amount of aldehyde which is used, secondary or tertiary amines are obtainable. Thus, the dimethylamino derivatives of formula (XLIb) are obtained by methylating compounds of formula (XL) with formaldehyde under reducing conditions.

In the formula (XLIa), $R_6$ preferably represents an alkyl group containing 1 to 5 carbon atoms, phenyl or a phenylalkyl group containing 7 or 8 carbon atoms.

In the formula (XLIb), alkyl groups $R_4$ and $R_{5'}$ preferably are lower alkyl groups containing 1 to 6, preferably 1 to 3, carbon atoms.

Subsequent to the introduction of amino groups a double bond in the 10,11-position of the compounds of formulae (XL) and (XLI) may be hydrogenated and/or a substituent in the 4-position may be further changed in order to obtain any other of the above defined substituents $R_2$ and $R_3$ according to the methods described above.

The compounds of formulae (XL) and (XLI) can be recovered in free form or in form of a salt. A salt form can easily be transferred into the free form and vice versa in conventional manners. Acid addition salts of compounds of formula (XL) and (XLI) can be formed with mineral acids such as, hydrochloric, hydrobromic, or sulfuric acid or with organic acids such as, maleinic or tartaric acid.

The compounds of formulae (XL) and (XLI) or their pharmaceutically acceptable salts may be formulated in conventional manners into pharmaceutical compositions optionally comprising an inert diluent and/or conventional pharmaceutical adjuvants.

The compounds of formulae (XL) and (XLI) and their pharmaceutically acceptable salts exhibit valuable pharmacological properties and therefore are useful in medical treatment. In particular, they are useful as sedatives since they exhibit sedative activities in animals as is indicated in standard tests, e.g., they inhibit the motility in mice upon oral administration of from 1 to 100 mg/kg body weight.

The compounds of formula (XLI) according to this invention, and their pharmaceutically acceptable salts are especially useful as soporific agents in the treatment of sleep disorders since they exhibit sleep-increasing and sleep-improving activities in animals as is indicated in standard tests. For example, they effect a significant increase of the duration of hexobarbital induced sleep in mice upon oral administration of from 1 to 100 mg/kg body weight.

For the above mentioned uses, the administered doses can vary considerably depending on the type of the compound, the animal, the mode of administration, the treated conditions and the therapy which is desired. Usually, satisfactory results are obtained with dosages between 0.075 and 100 mg/kg body weight. These doses can be administered internally, preferably orally, or parenterally. For example, daily oral doses for larger mammals can be chosen between 5 and 50 mg.

The invention will now be further described by the examples below. Not all of the compounds which are within the general scope of the compounds of formula (I) are mentioned below. Yet, in view of the general description of the invention and the conditions which are given in the working examples, anyone skilled in the art is enabled to obtain also those compounds within the scope of formula (I) which are not specifically cited below.

In the following description of the working examples, the 2,9-dioxatricyclo[4,3,1,0³,⁷] decane structure is abbreviated as "2,9-DTD".

Where the value "<0° C." is given as the melting point, this means that at room temperature, the compound is an oil.

EXAMPLE 1

Preparation of starting material:

Depending on which alcohol is used as a solvent and which hydrogen halide acid is used, the desired starting materials can be prepared according to the method described in the German Offenlegungsschrift No. 2,129,507, the disclosure of which is hereby incorporated by reference.

Thus, solutions of 850 g of an extract from valeriana wallichii DC, containing about 70% of dihydrovaltrate dissolved in methanol, ethanol and butanol are reacted each with a solution of hydrogen iodide dissolved in the same alcohol. In the case of a higher alcohol, it is advisable to allow the reaction mixture to stand at a temperature of about 80° C. for about 2 hours after addition of the hydrogen iodide. The following products are obtained:

(1.1)

3-iodomethyl-4β-acetoxy-8-methoxy-10-methylene-2,9-DTD (III):

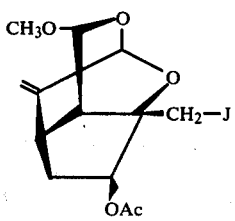

(III)

yield: 316 g
$C_{13}H_{17}O_5J$
molecular weight: 380.19
melting point: 104°–106° C.
$[\alpha]_D^{20}$: +68° (MeOH)

(1.2)
3-iodomethyl-4β-acetoxy-8-ethoxy-10-methylene-2,9-DTD (IV):

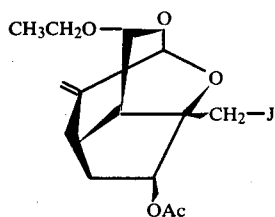

(IV)

yield: 296 g
$C_{14}H_{19}O_5J$
molecular weight: 394.2
melting point: 63°-65° C.
$[\alpha]_D^{20}$: +76° (MeOH)

(1.3)
3-iodomethyl-4β-acetoxy-8-n-butoxy-10-methylene-2,9-DTD (V):

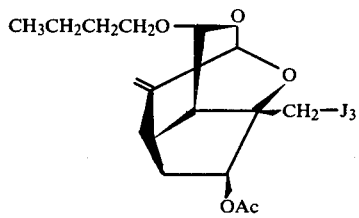

(V)

yield: 305 g
$C_{16}H_{23}O_5J$
molecular weight: 422.26
melting point: <0° C.
$[\alpha]_D^{20}$: +61° (MeOH)

EXAMPLE 2

Hydrogenation of the 10,11-double bond:

(2.1)
3-iodomethyl-4β-acetoxy-8-methoxy-10β-methyl-2,9-DTD (VI):

A solution of 800 g of 3-iodomethyl-4β-acetoxy-8-methoxy-10-methylene-2,9-dioxatricyclo[4,3,1,0^{3,7}] decane (III, Example 1.1) in 3 l of acetic acid ethyl ester is added to a suspension of 35 g of pre-hydrogenated platinum oxide in 300 ml of acetic acid ethyl ester. The mixture is hydrogenated at room temperature under normal pressure. The hydrogen uptake is fast in the beginning, yet towards the end, it becomes very slow. After the theoretical amount of hydrogen has been taken up (47.2 l), the reaction mixture is filtered over asbestos under a nitrogen atmosphere. After evaporating the solvent, 804 g of the raw product (=100% of the theoretical amount) are obtained. After repeated recrystallization of the product from methanol, 542 g of the pure 10β-methyl compound (=67% of the theoretical amount) are obtained.

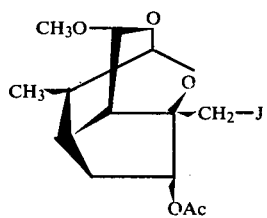

(VI)

$C_{13}H_{19}O_5J$
molecular weight: 382.19
melting point: 129°
$[\alpha]_D^{20}$: +24.5° (MeOH)

(2.2) 3-iodomethyl-4β-acetoxy-8-ethoxy-10β-methyl-2,9-DTD (VII) is prepared analogous to Example 2.1 from 73 g of 3-iodomethyl-4β-acetoxy-8-ethoxy-10-methylene-2,9-DTD (IV, Example 1.2) in the presence of 5 g of platinum oxide; yield 49.9 g (=68% of the theoretical amount) VII.

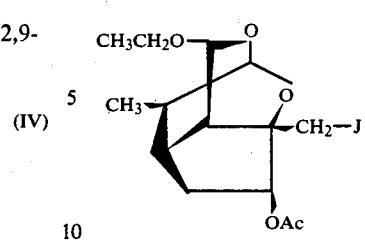

(VII)

$C_{14}H_{21}O_5J$
molecular weight: 396.228
melting point: 103°-105° C.
$[\alpha]_D^{20}$: +20.7° (MeOH)

(2.3) 3-iodomethyl-4β-acetoxy-8-n-butoxy-10β-methyl-2,9-DTD (VIII) is prepared analogous to Example 2.1 from 68 g of 3-iodomethyl-4β-acetoxy-8-n-butoxy-10-methylene-2,9-DTD (V, Example 1.3) in the presence of 2 g platinum oxide; yield 41 g ≙ 61% of the theoretical amount) VIII.

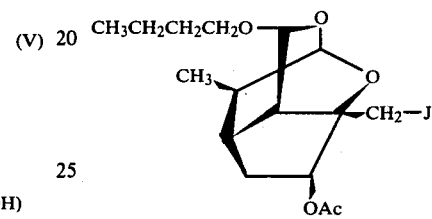

(VIII)

$C_{16}H_{25}O_5J$
molecular weight: 424
melting point: 60°-61° C.
$[\alpha]_D^{20}$: +12.9° (MeOH)

EXAMPLE 3

Introduction of the azido group:

(3.1) 10-methylene compounds:

(3.1.1)
3-azidomethyl-4β-acetoxy-8-methoxy-10-methylene-2,9-DTD (IX)

30 g of sodium azide are added to 14 g of 3-iodomethyl-4β-acetoxy-8-methoxy-10-methylene-2,9-dioxatricyclo[4,3,1,0^{3,7}] decane (III, Example 1.1) in 100 ml of hexamethyl-phosphoric acid triamide (HMPA) and the mixture is heated to 100° C. under stirring for 3 hours. Subsequently, 200 ml of ice water are added, and the solution is extracted six times with ether. The combined organic phases are once washed with water, dried over sodium sulfate, filtered and then evaporated to dryness under vacuum. After purifying the product over silica gel, using an n-hexane/ether mixture as a solvent, 10.55 g of IX (=96.8% of the theoretical amount) are obtained.

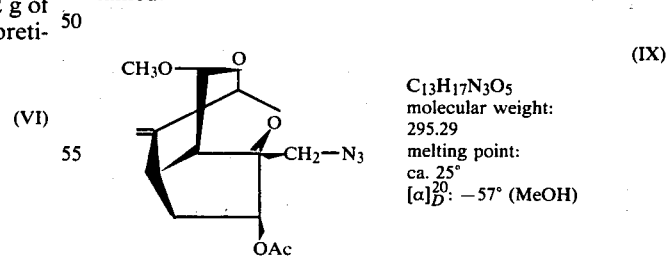

(IX)

$C_{13}H_{17}N_3O_5$
molecular weight: 295.29
melting point: ca. 25°
$[\alpha]_D^{20}$: −57° (MeOH)

(3.2) 10β-methyl compounds:

(3.2.1)
3-azidomethyl-4β-acetoxy-8-methoxy-10β-methyl-2,9-DTD (X):

50 g of 3-iodomethyl-4β-acetoxy-8-methoxy-10β-methyl-2,9-DTD (VI, Example 2.1) and 100 g of sodium azide in 150 ml of hexamethyl-phosphoric acid triamide (HMPA) are heated to 100° C. under stirring for 1 hour. Subsequently, 600 ml of ether are added to the reaction mixture and the mixture is shaken five times with 150 ml of water each. The combined washing waters are extracted with ether, and then the combined organic phases are dried over sodium sulfate, filtered, evaporated under vacuum and the resulting product is purified over silica gel using a mixture of n-hexane and ether as a solvent; yield 30.7 g (=79% of the theoretical amount).

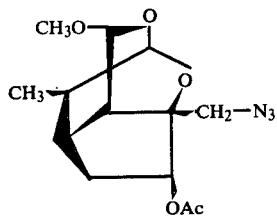

$C_{13}H_{19}O_5N_3$
molecular weight: 297.32
melting point: 37°–39° (from ether/n-hexane)
$[\alpha]_D^{20}$: +35° (MeOH)

(3.2.2) 3-azidomethyl-4β-acetoxy-8-ethoxy-10β-methyl-2,9-DTD (XI):

45 g of 3-iodomethyl-4β-acetoxy-8-ethoxy-10β-methyl 2,9-dioxatricyclo[4,3,1,0³,⁷] decane (VII, Example 2.2) are dissolved in 150 ml of hexamethyl-phosphoric acid triamide and 90 g of sodium azide are added. The suspension is stirred at a temperature of 100° C. for 1 hour. Subsequently, water is added, and the solution is extracted with ether. The combined organic phases are dried over sodium sulfate, filtered and evaporated under vacuum. After purifying the product over silica gel using an n-hexane/ether mixture as a solvent, 31 g (=87.5% of the theoretical amount) are obtained.

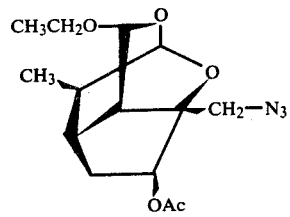

(XI)

$C_{14}H_{21}O_5N_2$
molecular weight: 311.34
melting point: <0° C.
$[\alpha]_D^{20}$: +21° (MeOH)

(3.2.3) 3-azidomethyl-4β-acetoxy-8-n-butoxy-10β-methyl-2,9-DTD (XII) is prepared analogous to Example 3.2.1, or 3.2.2, from 3-iodomethyl-4β-acetoxy-8-n-butoxy-10β-methyl-2,9-DTD (VIII, Example 2.3).

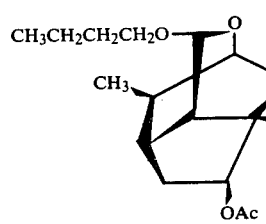

(XII)

$C_{16}H_{25}N_3O_5$
molecular weight: 339
melting point: <0°
$[\alpha]_D^{20}$: +11.1° (MeOH)

The compounds (IX), (X), (XI) and (XII) according to the four examples above, are final products wherein $R_2$ equals acetoxy.

EXAMPLE 4

Hydrolysis of the 4β-acetoxy group:

(4.1) 10-methylene compounds:

(4.1.1) 3-azidomethyl-4β-hydroxy-8-methoxy-10-methylene-2,9-DTD (XIII):

1.45 g of sodium hydroxide in 20 ml of methanol are added to 10.50 g of 3-azidomethyl-4β-acetoxy-8-methoxy-10-methylene-2,9-DTD (IX, Example 3.1.1) in 100 ml of ether and the reaction mixture is stirred for 1 hour at room temperature. Subsequently, the mixture is neutralized with glacial acetic acid and the solution is washed with water. After extracting the aqueous phase with ether, the combined organic phases are dried over sodium sulfate, filtered and evaporated under vacuum: yield 8.8 g (=98% of the theoretical amount).

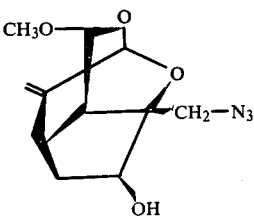

(XIII)

$C_{11}H_{15}N_3O_4$
molecular weight: 253.26
melting point: <0°
$[\alpha]_D^{20}$: +10° (MeOH)

(4.2) 10β-methyl compounds:

(4.2.1) 3-azidomethyl-4β-hydroxy-8-methoxy-10β-methyl-2,9-DTD (XIV)

A mixture of 16 g of 3-azidomethyl-4β-acetoxy-8-methoxy-10β-methyl-2,9-DTD (X, Example 3.2.1) in 200 ml of ether, and 1.6 g of sodium hydroxide in 50 ml of methanol are stirred for 10 minutes at room temperature. Subsequently, ice water is added and the mixture is neutralized with glacial acetic acid. Then, the solution is extracted with ether. The combined organic phases are dried over sodium sulfate, filtered and evaporated under vacuum. After purification of the product over silica gel, using an n-hexane/ether mixture as a solvent, 12.5 g of a colorless oil (=90.6% of the theoretical amount) are obtained.

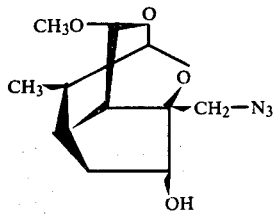

(XIV)

$C_{11}H_{17}N_3O_4$
molecular weight: 255.28
melting point: <0°
$[\alpha]_D^{20}$: −66.6° (MeOH)

(4.2.2) 3-azidomethyl-4β-hydroxy-8-ethoxy-10β-methyl-2,9-DTD (XV):

3.1 g of sodium hydroxide in 100 ml of ethanol are added to 24 g of 3-azidomethyl-4β-acetoxy-8-ethoxy-10β-methyl-2,9-DTD (XI, Example 3.2.2) in 250 ml of ether, and the solution is stirred for 15 minutes at room temperature. Subsequently, the solution is poured into ice water, and the mixture is extracted with ether. The combined organic phases are dried over sodium sulfate, filtered and evaporated under vacuum. After purifying the product over silica gel, using n-hexane/ether as a solvent, the yield is 30.2 g (=97.5% of the theoretical amount).

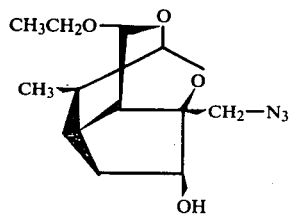

(XV)

$C_{12}H_{19}O_4N_3$
molecular weight: 269.31
melting point: <0°
$[\alpha]_D^{20}$: −64.2° (MeOH)

(4.2.3) 3-azidomethyl-4β-hydroxy-8-n-butoxy-10β-methyl-2,9-DTD (XVI) is prepared analogous to Example 4.2.1, or 4.2.2, from 3-azidomethyl-4β-acetoxy-8-n-butoxy-10β-methyl-2,9-DTD (XII, Example 3.2.3):

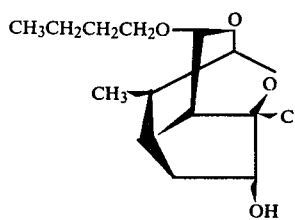

(XVI)

$C_{14}H_{23}N_3O_4$
molecular weight: 297
melting point: <0°
$[\alpha]_D^{20}$: −67.7° (MeOH)

EXAMPLE 5

Oxidation of the 4β-hydroxy group to form the decane-4-one:

(5.1) 10-methylene compounds:

(5.1.1)
3-azidomethyl-8-methoxy-10-methylene-2,9-DTD-4-one (XVII)

8.8 g of 3-azidomethyl-4β-hydroxy-8-methoxy-10-methylene-2,9-DTD (XIII, Example 4.1.1) are dissolved in 100 ml of acetone. 20 ml of Jones-reagent are added dropwise and the mixture is stirred for about 3 hours at a temperature of 0° C. Subsequently, 3 ml of isopropanol are added to the reaction mixture, and the precipitated chromium salts are filtered off. The filtrate is neutralized with sodium carbonate, then water is added, and the mixture is extracted with methylene chloride. The combined organic phases are dried over sodium sulfate, filtered, and evaporated under vacuum. After purifying the product over silica gel using an n-hexane/ether mixture as a solvent, 6.83 g of (XVII) (=78.2% of the theoretical amount) are obtained.

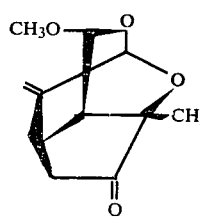

(XVII)

$C_{11}H_{13}N_3O_4$
molecular weight: 251.24
melting point: 46°-49°
$[\alpha]_D^{20}$: −29° (MeOH)

(5.2) 10β-methyl compounds:

(5.2.1)
3-azidomethyl-8-methoxy-10β-methyl-2,9-DTD-4-one (XVIII):

To a solution of 16 g of 3-azidomethyl-4β-hydroxy-8-methoxy-10β-methyl-2,9-DTD (XIV, Example 4.2.1) in 300 ml of acetone, 40 ml of a CrO_3-solution (Jones-reagent) are slowly added at a temperature of 0° C. Subsequently, 10 ml of isopropanol are added, the precipitated chromium salts are filtered off, and the precipitate is washed with methylene chloride. The combined organic phases are neutralized with a sodium carbonate solution, and then washed with water. After drying over sodium sulfate and filtering, the filtrate is evaporated under vacuum. After purifying the product over silica gel using an n-hexane/ether mixture as a solvent, 13.8 g are obtained (=76.5% of the theoretical amount).

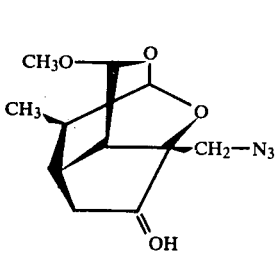

(XVIII)

$C_{11}H_{15}N_3O_4$
molecular weight: 253.26
melting point: 51°-55°
$[\alpha]_D^{20}$: −90.2° (MeOH)

(5.2.2)
3-azidomethyl-8-ethoxy-10β-methyl-2,9-DTD-4-one (XIX):

To a solution of 16 g of 3-azidomethyl-4β-hydroxy-8-ethoxy-10β-methyl-2,9-DTD (XV, Example 4.2.2) in 300 ml of acetone, 40 ml of Jones reagent are added at a temperature of 0° C. Subequently, the reaction mixture is neutralized with a sodium carbonate solution and extracted with methylene chloride. The combined organic phases are dried over sodium sulfate, filtered, and evaporated under vacuum. After purifying the product over a silica gel using an n-hexane/ether mixture as a solvent, 12.2 g are obtained (=76.8% of the theoretical amount).

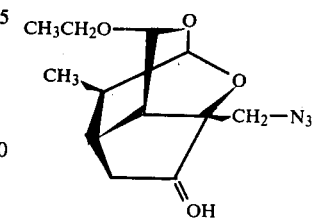

(XIX)

$C_{12}H_{17}N_3O_4$
molecular weight: 267.29
melting point: β°-63° C.
$[\alpha]_D^{20}$: −92.8° (MeOH)

(5.2.3) 3-azidomethyl-8-n-butoxy-10β-methyl-2,9-DTD-4-one (XX) is prepared analogous to Example 5.2.1 or 5.2.2 from 3-azidomethyl-4β-hydroxy-8-n-butoxy-10β-methyl-2,9-DTD (XVI, Example 4.2.3):

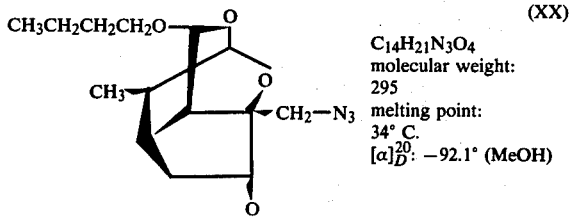

(XX)

C₁₄H₂₁N₃O₄
molecular weight: 295
melting point: 34° C.
$[\alpha]_D^{20}$: −92.1° (MeOH)

EXAMPLE 6

Reduction of the decane-4-one into the 4α-hydroxy compound:

(6.1) 10-methylene compounds:

(6.1.1)
3-azidomethyl-4α-hydroxy-8-methoxy-10-methylene-DTD (XXI):

To a solution of 3 g of 3-azidomethyl-8-methoxy-10-methylene-2,9-DTD-4-one (XVII, Example 5.1.1) in 20 ml of absolute ether, 1 g of LiBH₄ is added portionwise under nitrogen atmosphere at a temperature of 0° C. After 30 minutes, moist ether, and subsequently water are added. The ether phase is separated, dried over sodium sulfate, filtered and evaporated under vacuum. Yield 2.3 g (=76.2% of the theoretical amount).

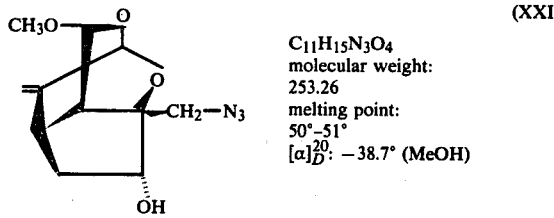

(XXI)

C₁₁H₁₅N₃O₄
molecular weight: 253.26
melting point: 50°–51°
$[\alpha]_D^{20}$: −38.7° (MeOH)

(6.2) 10β-methyl compounds:

(6.2.1)
3-azidomethyl-4α-hydroxy-8-methoxy-10β-methyl-2,9-DTD (XXII):

To a suspension of 1.5 g of LiBH₄ in 100 ml of absolute tetrahydrofurane, 12.7 g of 3-azidomethyl-8-methoxy-10β-methyl-2,9-DTD-4-one (XVIII, Example 5.2.1) in 100 ml of absolute tetrahydrofurane are added dropwise under nitrogen atmosphere and cooled with ice. After 30 minutes moist ether, and subsequently water, are added. The ether phase is separated, and then is dried over sodium sulfate, filtered and evaporated under vacuum. After purifying the product over silica gel using n-hexane/ether as a solvent, and subsequently recrystallizing it, 10.6 g of (XIV) are obtained (=83% of the theoretical amount).

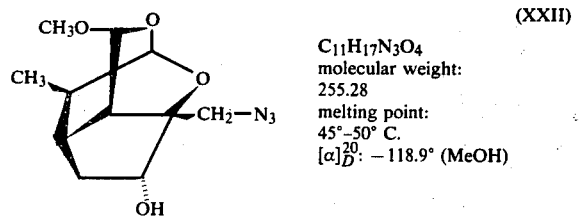

(XXII)

C₁₁H₁₇N₃O₄
molecular weight: 255.28
melting point: 45°–50° C.
$[\alpha]_D^{20}$: −118.9° (MeOH)

(6.2.2)
3-azidomethyl-4α-hydroxy-8-ethoxy-10β-methyl-2,9-DTD (XXIII):

To a suspension of 1.5 g of LiBH₄ in 100 ml of absolute tetrahydrofurane, 12.67 g of 3-azidomethyl-8-ethoxy-10β-methyl-2,9-dioxatricyclo[4,3,1,0³,⁷]decane-4-one (XIX, Example 5.2.2) in 100 ml of absolute tetrahydrofurane are added dropwise under nitrogen atmosphere at a temperature 0° C. After 30 minutes, moist ether, and subsequently water are added. After extracting with ether, the combined organic phases are dried over sodium sulfate, filtered and evaporated under vacuum. After purifying the product over silica gel using an n-hexane/ether mixture as a solvent, 10.63 g (=83% of the theoretical amount) are obtained.

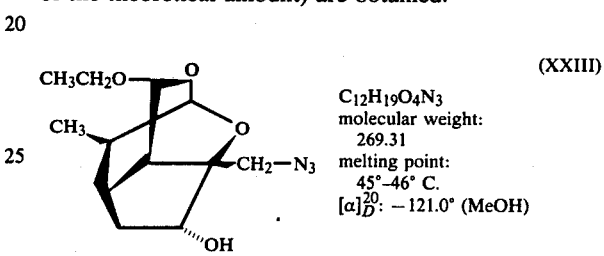

(XXIII)

C₁₂H₁₉O₄N₃
molecular weight: 269.31
melting point: 45°–46° C.
$[\alpha]_D^{20}$: −121.0° (MeOH)

(6.2.3) 3-azidomethyl-4α-hydroxy-8-n-butoxy-10β-methyl-2,9-DTD (XXIV) is prepared analogous to Example 6.2.1 or 6.2.2, from 3-azidomethyl-8-n-butoxy-10β-methyl-2,9-DTD-4-one (XX, Example 5.2.3).

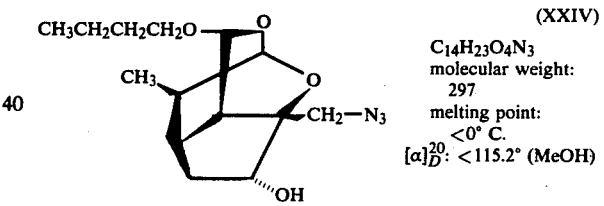

(XXIV)

C₁₄H₂₃O₄N₃
molecular weight: 297
melting point: <0° C.
$[\alpha]_D^{20}$: <115.2° (MeOH)

EXAMPLE 7

Transformation of the 4α-hydroxy group into an ester or carbamate group:

(7.1) Ester (7.1.1)
3-azidomethyl-4α-acetoxy-8-methoxy-10-methylene-2,9-DTD (XXV):

To a solution of 5.4 g 3-azidomethyl-4α-hydroxy-8-methoxy-10-methylene-2,0-DTD (XXI, Example 6.1.1) in 5 ml of pyridine, 5 ml of acetic acid anhydride are added and the solution is heated to 60° C. under stirring. After one hour, the solution is repeatedly evaporated under vacuum under addition of ethanol, dissolved in ether, and shaken with water. The aqueous phase is neutralized with sodium carbonate and extracted with ether. The combined organic phases are dried over sodium sulfate, filtered, and evaporated under vacuum. Yield 6.38 g (=85.8% of the theoretical amount).

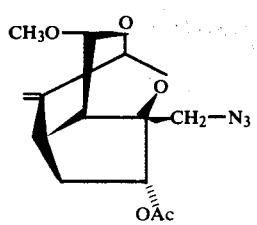

(XXV)

C$_{13}$H$_{17}$N$_3$O$_5$
molecular weight: 295.29
melting point: <0°
$[\alpha]_D^{20}$: +30.1° (MeOH)

(7.1.2)
3-azidomethyl-4α-acetoxy-8-methoxy-10β-methyl-2,9-DTD (XXVI):

1 ml of acetic acid anhydride is added to 1 g of 3-azidomethyl-4α-hydroxy-8-methoxy-10β-methyl-2,9-DTD (XXII, Example 6.2.1) in 2 ml of pyridine, and the reaction mixture is allowed to stand at room temperature over night. Subsequently, the solution is repeatedly evaporated to dryness under addition of ethanol. After the product has been purified over silica gel, using an n-hexane/ether mixture as a solvent, 0.93 g of (XI) (=80% of the theoretical amount) are obtained.

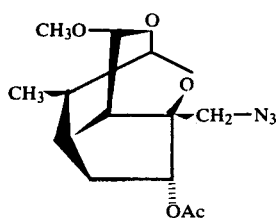

(XXVI)

C$_{13}$H$_{19}$O$_5$N$_3$
molecular weight: 297.32
melting point: <0°
$[\alpha]_D^{20}$: −35.3° (MeOH)

(7.1.3)
3-azidomethyl-4α-acetoxy-8-ethoxy-10β-methyl-2,9-DTD (XXVII):

1 ml of acetic anhydride are added to 1 g of 3-azidomethyl-4α-hydroxy-8-ethoxy-10β-methyl-2,9-DTD (XXIII, Example 6.2.2) in 2 ml of pyridine, and the reaction mixture is allowed to stand at room temperature for 18 hours. Subsequently, the mixture is repeatedly evaporated to dryness under addition of ethanol. The raw product is purified over silica gel, using an n-hexane/ether mixture as a solvent. Yield 1.16 g (=80% of the theoretical amount).

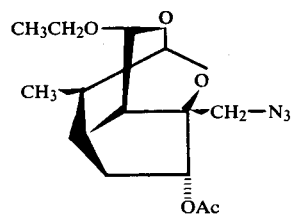

(XXVII)

C$_{14}$H$_{21}$O$_5$N$_3$
molecular weight: 311.34
$[\alpha]_D^{20}$: −42.7° (MeOH)

(7.1.4) 3-azidomethyl-4α-acetoxy-8-n-butoxy-10β-methyl-2,9-DTD (XXVIII) is prepared analogous to Examples 7.1.1 to 7.1.3, from 3-azidomethyl-4α-hydroxy-8-n-butoxy-2,9-DTD (XXIV, Example 6.2.3):

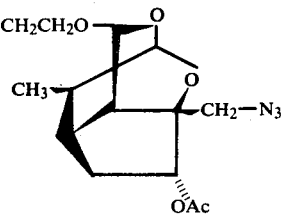

(XXVIII)

C$_{16}$H$_{25}$N$_3$O$_3$
molecular weight: 239.4
melting point: <0° C.
$[\alpha]_D^{20}$: −45.4° (MeOH)

(7.2) Carbamates:

(7.2.1)
3-azidomethyl-4α-methylcarbamoyloxy-8-methoxy-10β-methyl-2,9-DTD (XXIX):

To a solution of 0.6 g 3-azidomethyl-4α-hydroxy-8-methoxy-10β-methyl-2,9-DTD (XXII, Example 6.2.1) in 10 ml of toluene, 0.5 ml of methylisocyanate and a small amount of phenyl mercury acetate are added, and the mixture is refluxed for 1 hour. Subsequently, the mixture is repeatedly evaporated to dryness under vacuum under addition of toluene. The residue is dissolved in ether and once shaken with water. The ether phase is dried over sodium sulfate, filtered and evaporated under vacuum.

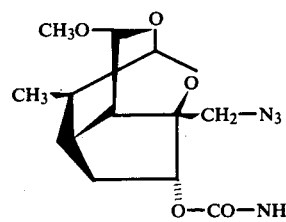

(XXIX)

C$_{13}$H$_{20}$N$_4$O$_5$
molecular weight: 312.332
melting point: <0°
$[\alpha]_D^{20}$: −40.9° (MeOH)

Analogous to Example 7.2.1, the following compounds are prepared:

(7.2.2)
3-azidomethyl-4α-n-butylcarbamoyloxy-8-methoxy-10β-methyl-2,9-DTD (XXX):

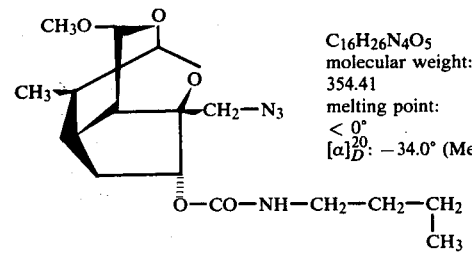

(XXX)

C$_{16}$H$_{26}$N$_4$O$_5$
molecular weight: 354.41
melting point: <0°
$[\alpha]_D^{20}$: −34.0° (MeOH)

(7.2.3) 3-azidomethyl-4α-methylcarbamoyloxy-8-ethoxy-10β-methyl-2,9-DTD (XXXI):

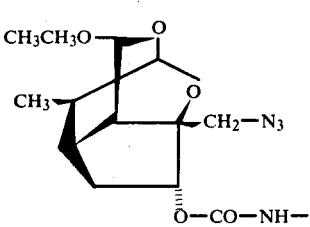

(XXXI)

C$_{14}$H$_{22}$N$_4$O$_5$
molecular weight: 326.358
melting point: <0°
$[\alpha]_D^{20}$: −43.2° (MeOH)

(7.2.4) 3-azidomethyl-4α-n-butylcarbamoyloxy-8-ethoxy-10β-methyl-2,9-DTD (XXXII):

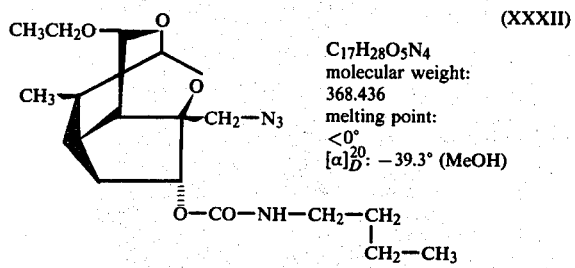

(XXXII)

C$_{17}$H$_{28}$O$_5$N$_4$
molecular weight: 368.436
melting point: <0°
[α]$_D^{20}$: −39.3° (MeOH)

(7.2.5) 3-azidomethyl-4α-methylcarbamoyloxy-8-n-butoxy-10β-methyl-2,9-DTD (XXXIII):

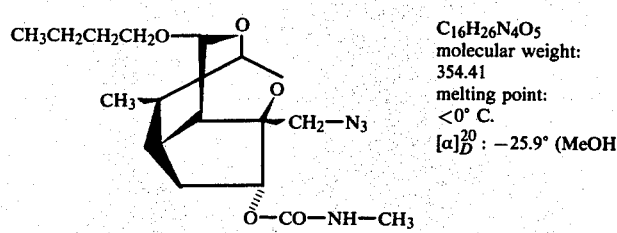

(XXXIII)

C$_{16}$H$_{26}$N$_4$O$_5$
molecular weight: 354.41
melting point: <0° C.
[α]$_D^{20}$: −25.9° (MeOH)

EXAMPLE 8
CAPSULES FOR ORAL APPLICATION

| | |
|---|---|
| 3-azidomethyl-4α-acetoxy-8-methoxy-10β-methyl-2,9-dioxatricyclo[4,3,1,0$^{3,7}$] decane | 20 g |
| lactose | 60 g |
| starch | 18.5 g |
| magnesium stearate | 1.5 g |

The components are thoroughly mixed and the mixture is filled into gelatin capsules in portions of 100 mg per capsule.

EXAMPLE 9

One capsule, which is prepared according to Example 8, is administered to an adult person once a day for the treatment of pains.

EXAMPLE 10

Preparation of 3-aminomethyl-4β-hydroxy-8-methoxy-10-methylene-2,9-dioxatricyclo[4,3,1,0$^{3,7}$] decane (XLII) from 3-azidomethyl-4β-hydroxy-8-methoxy-10-methylene-2,9-dioxatricyclo[4,3,1,0$^{3,7}$] decane (XIII):

17.7 g of 3-azidomethyl-4β-hydroxy-8-methoxy-10-methylene-2,9-dioxatricyclo[4,3,1,0$^{3,7}$] decane are dissolved in 700 ml of methanol and 35 ml of hydrazine hydrate (contents 80%) are added. Then about 1 g of Rainey nickel is added and the mixture is allowed to stand at room temperature for 1 hour. Then the catalyst is sucked off over asbestos and the filtrate is evaporated at 50° C. under reduced pressure which is produced by a water jet pump. Benzene is added to the residue, then it is filtered, the solvent is evaporated and the remaining residue is recrystallized from ether. 15.3 g of colorless crystals are obtained. This corresponds to 94.6% of the theoretically obtainable amount.

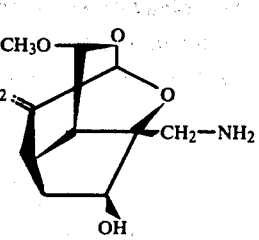

(XLII)

Empirical formula: C$_{11}$H$_{17}$NO$_4$
Molecular weight: 227.26
mp.: 108°–109° C.
[α]$_D^{25}$ = −37° C. in methanol

EXAMPLE 11

Preparation of 3-aminomethyl-4β-hydroxy-8-methoxy-10-methyl-2,9-dioxatricyclo[4,3,1,0$^{3,7}$] decane (XLIII) from 3-azidomethyl-4β-hydroxy-8-methoxy-10-methyl-2,9-dioxatricyclo[4,3,1,0$^{3,7}$] decane (XIV).

To 10.7 g of 3-azidomethyl-4β-hydroxy-8-methoxy-10-methyl-2,9-dioxatricyclo[4,3,1,0$^{3,7}$] decane in 200 ml of methanol, 32 ml of hydrazine hydrate (contents 80%) are added. Then 1 g of Rainey nickel in 100 ml of methanol is added and the mixture is stirred at room temperature for 1 hour. The catalyst is filtered off and the filtrate is evaporated to dryness under vacuum. Water is added to the residue, the mixture is alkalized and subsequently extracted with ether. The united etherical phases are dried over sodium sulfate, filtered and evaporated at 40° C. under vacuum. 9.1 g of a colorless oil are obtained. This corresponds to 94.3% of the theoretically obtainable amount.

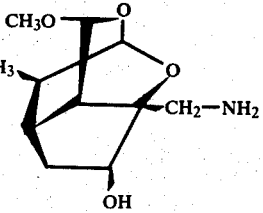

(XLIII)

Empirical formula: C$_{11}$H$_{19}$NO$_4$
Molecular weight: 229.28
[α]$_D^{22}$ −9° in methanol

EXAMPLE 12

Preparation of 3-N,N-dimethylaminomethyl-4β-hydroxy-8-methoxy-10-methyl-2,9-dioxatricyclo[4,3,1,0$^{3,7}$] decane (XLIV) from 3-aminomethyl-4β-hydroxy-8-methoxy-10-methyl-2,9-dioxatricyclo[4,3,1,0$^{3,7}$] decane (XLII).

To 800 mg of 3-aminomethyl-4β-hydroxy-8-methoxy-10-methyl-2,9-dioxatricyclo[4,3,1,0$^{3,7}$] decane in 5 ml of methanol, 5 ml of a 37% formaldehyde solution are added and the mixture is stirred at room temperature for about 10 minutes. A small amount (e.g., about as much as would be borne on the tip of a spatula) of Rainey nickel is added and the mixture is hydrogenated at room temperature. When the hydrogen uptake is finished, the catalyst is filtered off and the filtrates is evaporated to dryness.

The residue is purified over silica gel using chloroform/methanol as a solvent. 780 mg of the substance are obtained. This corresponds to 86.9% of the theoretically obtainable amount.

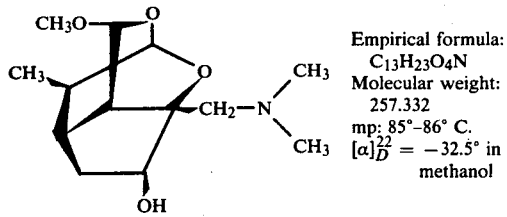

(XLIV)

Empirical formula: $C_{13}H_{23}O_4N$
Molecular weight: 257.332
mp: 85°–86° C.
$[\alpha]_D^{22} = -32.5°$ in methanol

What is claimed is:

1. A compound selected from the group of 3-aminomethyl-2,9-dioxatricyclo[4,3,1,0$^{3,7}$] decanes of the formula XL

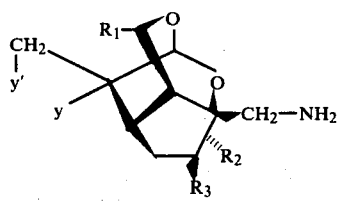

(XL)

wherein:

$R_1$ represents alkyloxy or aralkyloxy;

one of $R_2$ and $R_3$ is hydrogen and the other represents hydroxy, acyloxy, or carbamyloxy, or $R_2$ and $R_3$ jointly represent oxygen; and y and y' each represent hydrogen or jointly form a bond.

2. The compounds as defined in claim 1 wherein one of $R_2$ and $R_3$ is hydrogen and the other represents hydroxy, an acyloxy group Z—COO— wherein Z is an alkyl- or a carbamyloxy group Z—NHCOO— wherein Z is an alkyl- or alkenylrest containing 1 to 4 carbon atoms or a phenylrest, or $R_2$ and $R_3$ jointly represent oxygen.

3. The compound as defined in claim 1 wherein $R_1$ represents an alkoxy group containing 1 to 6 carbon atoms or an aralkyloxy group containing 7 to 9 carbon atoms.

4. The compounds as defined in claim 1 wherein the y'—CH$_2$- group represents a 10β-methyl group and y is hydrogen.

5. The compounds as defined in claim 3 wherein $R_1$ is methoxy.

6. The compounds as defined in claim 2 wherein one of $R_2$ and $R_3$ is hydrogen and the other represents acetoxy.

7. The compound as desired in claim 1 which is 3-aminomethyl-4β-hydroxy-8-methoxy-10-methyl-2,9-dioxatricyclo[4,3,1,0$^{3,7}$] decane.

8. A pharmaceutical composition for sedating larger mammals comprising an inert carrier material and a sedatively effective amount of a compound as defined in claim 1.

9. A method for sedating larger mammals, which comprises the step of administering to a larger mammal a sedatively effective amount of a compound as defined in claim 1.

* * * * *